United States Patent
Lee et al.

(10) Patent No.: US 11,488,709 B2
(45) Date of Patent: Nov. 1, 2022

(54) APPARATUS AND METHOD FOR DELIVERY-CONTEMPORANEOUS MEDICINE VERIFICATION

(71) Applicant: Zyno Medical, LLC, Natick, MA (US)

(72) Inventors: Chao Young Lee, Weston, MA (US); Mei Zhang, Sharon, MA (US)

(73) Assignee: Zyno Medical, LLC, Natick, MA (US)

( * ) Notice: Subject to any disclaimer, the term of this patent is extended or adjusted under 35 U.S.C. 154(b) by 990 days.

(21) Appl. No.: 15/410,020

(22) Filed: Jan. 19, 2017

(65) Prior Publication Data
US 2017/0206336 A1 Jul. 20, 2017

Related U.S. Application Data

(60) Provisional application No. 62/280,999, filed on Jan. 20, 2016.

(51) Int. Cl.
| | | |
|---|---|---|
| *G16H 40/67* | (2018.01) | |
| *G16H 10/60* | (2018.01) | |
| *G16H 40/63* | (2018.01) | |
| *G16H 20/17* | (2018.01) | |
| *G16H 70/40* | (2018.01) | |
| *G16C 20/20* | (2019.01) | |

(52) U.S. Cl.
CPC ............ *G16H 40/67* (2018.01); *G16H 10/60* (2018.01); *G16H 20/17* (2018.01); *G16H 40/63* (2018.01); *G16H 70/40* (2018.01); *G16C 20/20* (2019.02)

(58) Field of Classification Search
CPC ... G06F 19/3468; G06F 19/326; G16H 20/17; G16H 10/60; G16H 70/40; G16H 40/63; G16C 20/20
See application file for complete search history.

(56) References Cited

U.S. PATENT DOCUMENTS

| 6,111,639 A * | 8/2000 | Reduto ................ G01J 3/02 356/300 |
| 8,386,070 B2 | 2/2013 | Eliuk et al. |
| 8,652,093 B2 | 2/2014 | Guo et al. |
| 8,945,043 B2 | 2/2015 | Lee et al. |

(Continued)

FOREIGN PATENT DOCUMENTS

| JP | 2005066272 | 3/2005 |
| JP | 2005066272 A * | 3/2005 |

(Continued)

OTHER PUBLICATIONS

Choi, Charles J. "Nanodome Sensor Tubing for Monitoring of Intravenous Drug Infusion and Metabolites" 2011 11th IEEE International Conference on Nanotechnology, Portland, OR, 2011, pp. 161-165. (Year: 2011).*

(Continued)

*Primary Examiner* — Robert W Morgan
*Assistant Examiner* — Chance L Smith
(74) *Attorney, Agent, or Firm* — Boyle Fredrickson S.C.

(57) ABSTRACT

A device for providing drug verification may work in conjunction with drug delivery devices such as medical pumps to provide a chemical and concentration analysis of drugs being delivered forming a signature that can be compared to a signature associated with the proper drug, reducing errors in medicine delivery and ensuring proper use of medicines throughout their lifecycle.

19 Claims, 5 Drawing Sheets

(56) References Cited

U.S. PATENT DOCUMENTS

| | | |
|---|---|---|
| 9,242,037 B2 | 1/2016 | Zhang et al. |
| 9,327,072 B2 | 5/2016 | Zhang et al. |
| 9,375,531 B2 | 6/2016 | Lee et al. |
| 9,378,334 B2 | 6/2016 | Lee et al. |
| 9,446,191 B2 | 9/2016 | Zhang et al. |
| 2002/0038392 A1* | 3/2002 | De La Huerga .... G06F 19/3468 710/8 |
| 2003/0204330 A1* | 10/2003 | Allgeyer .............. A61B 5/0059 702/32 |
| 2004/0172302 A1* | 9/2004 | Martucci ............ G06F 19/3418 705/2 |
| 2005/0099624 A1* | 5/2005 | Staehr ............... A61M 5/14212 356/319 |
| 2005/0261940 A1* | 11/2005 | Gay ..................... G06Q 10/087 705/3 |
| 2006/0160238 A1* | 7/2006 | Lennernas ............. G01N 21/31 436/164 |
| 2006/0259195 A1 | 11/2006 | Eliuk et al. |
| 2007/0008523 A1* | 1/2007 | Kaye ..................... B07C 5/344 356/300 |
| 2007/0201025 A1* | 8/2007 | Greenwald ......... G06F 19/3468 356/319 |
| 2012/0125998 A1 | 5/2012 | Magill |
| 2012/0222468 A1 | 9/2012 | Nelson et al. |
| 2012/0226446 A1* | 9/2012 | Nelson .................. G16H 40/60 702/25 |
| 2012/0276549 A1 | 11/2012 | Cunningham et al. |
| 2012/0283630 A1 | 11/2012 | Lee et al. |
| 2013/0144206 A1 | 6/2013 | Lee et al. |
| 2014/0114238 A1* | 4/2014 | Lee .................. A61M 5/16804 604/67 |
| 2014/0194817 A1 | 7/2014 | Lee et al. |
| 2015/0165118 A1 | 6/2015 | Lee et al. |
| 2016/0030683 A1* | 2/2016 | Taylor .................... A61M 5/32 604/151 |
| 2016/0136354 A1 | 5/2016 | Zhang et al. |
| 2017/0132374 A1 | 5/2017 | Lee et al. |

FOREIGN PATENT DOCUMENTS

| | | | |
|---|---|---|---|
| WO | 2004109262 A1 | 12/2004 | |
| WO | WO-2013189860 A2 * | 12/2013 | ............ A61M 5/142 |
| WO | 2014152704 | 9/2014 | |

OTHER PUBLICATIONS

EP Search Report dated Jul. 28, 2017 in corresponding EP App. No. 17152254.3.

Choi et al., "Nandome Sensor Tubing for Monitoring of Intravenous Drug infusion and Metabolites", 2011 11th IEEE Conference, Aug. 15, 2011, pp. 161-165.

* cited by examiner

APPARATUS AND METHOD FOR DELIVERY-CONTEMPORANEOUS MEDICINE VERIFICATION

CROSS REFERENCE TO RELATED APPLICATION

This application claims the benefit of U.S. provisional application 62/280,999 filed Jan. 20, 2016 and hereby incorporated by reference.

BACKGROUND OF THE INVENTION

The present invention relates to medical systems that may monitor and manage patients and patient treatment, and in particular to a system for confirming proper medicine type and medicine formulation contemporaneous with the delivery of that medicine to the patient.

The delivery of medicines, for example, in a hospital or other healthcare setting, is an important yet challenging part of healthcare management. It is essential not only that the correct medicines be delivered to the proper patients but also that a particular formulation of the medicine, for example, the medicine concentration, be correct.

Some medicines, such as painkillers, may be subject to misuse and accordingly their formulation and delivery must be monitored with particular care. Normally, such monitoring involves careful recording of the dispensing of the medicine, for example, from a central pharmacy and properly labeling the medicine containers so dispensed. Yet after the dispensing of the medicine, there can be a substantial delay before the medicine is delivered to the patient raising opportunities for mix-up, loss or diversion of the medicine. To address these latter problems, normally the attending healthcare professional, for example, a nurse at bedside, is relied upon to confirm that the proper medicine and proper medicine concentration is being delivered to the proper patient. This endpoint confirmation may be ineffective in cases where the medicine was incorrectly labeled or identified when delivered to the pharmacy or where the label on the dispensing container has been altered or is an error, or where the contents of the medicine container have been manipulated after dispensing, or where the healthcare professional deliberately or mistakenly authorizes the incorrect medicine or medicine concentration.

Ideally medicines might be tested immediately before delivery to the patient, however, the equipment and techniques necessary to accurately analyze and uniquely characterize medicines in such settings would be prohibitively expensive.

SUMMARY OF THE INVENTION

The present inventors have recognized that the goal of reducing medication errors can be largely met by characterizing the medicines according to "signatures" that uniquely characterize their chemical content or formulation. Such signatures can be readily generated at the point-of-delivery by compact automated sensor systems such as Raman spectrometers. Although the medicine cannot be directly identified in the sense of a complete chemical analysis, the characterization provided by the signature operates effectively to deter or detect medication errors.

Accordingly, one embodiment of the present invention provides a system for automatic verification of medicine type and/or concentration contemporaneous with the delivery of the medicine to the patient. In one embodiment, a medicine signature sensor is incorporated into the medical pump delivering the medicine to the patient so that real time medicine type and formulation information can be verified. In an alternative embodiment, a similar medicine signature sensor is provided in a freestanding appliance shared among spatially proximate delivery pumps to provide contemporaneous verification.

In both cases, by independently assessing the medicine characteristics at the latest possible moment before delivery to the patient, the present invention address a wide range of tampering or other errors that can occur during and after dispensing of the medicine but before delivery to the patient. By taking advantage of a central medical database indicating the type of drug intended to be delivered to the patient, an automated medicine signature sensor becomes practical, needing only to distinguish between specific categories of drugs and formulations rather than providing a full chemical analysis. A trade-off between false positive error detection and comprehensive elimination of errors can be flexibly implemented.

Specifically, in one embodiment, the invention provides a point-of-delivery drug verification apparatus having a sensor system adapted to analyze a drug in a package for delivery to a patient to establish a measured drug signature dependent on the formulation of the drug. The drug verification apparatus also has an input for receiving a nominal identity of the drug in the package linked to the package. The measured drug signature is a function of chemical formulation of the drug. An electronic computer executes a stored program to: (1) receive the nominal identity of the drug to determine a correct drug signature associated with the drug and to compare the correct drug signature with the measured drug signature: and (2) provide an output indicating if the correct drug signature differs from the measured drug signature by a predetermined amount.

It is thus a feature of at least one embodiment of the invention to provide a point-of-delivery auditing of medication addressing a variety of possible sources of medication error.

It is also a feature of at least one embodiment of the mention to provide the benefits point-of-delivery auditing using achievable current technology recognizing that successful auditing need not require a comprehensive chemical analysis.

The point-of-delivery drug verification apparatus may further include a scale for measuring a weight of the drug and the measured signature and correct signature may include weight components.

It is thus a feature of at least one embodiment of the invention provide a signature that reflects drug concentration.

The correct ding signature and measured drug signature may be a function of both chemical formulation and concentration of the drug.

It is thus a feature of at least one embodiment of the invention to provide an, auditing both as to the chemical formulation of the medicine but also its amount (possibly a combination of concentration and weight) to detect not only medication type errors but also dosage or diversion issues.

The sensor may be a spectrometer.

It is thus a feature of at least one embodiment of the invention to provide sophisticated chemical analysis of a contain drug amenable to non-contact measurements, for example, through an IV tube.

The spectrometer may be selected from the group consisting of: Raman spectrometers, surface enhanced Raman spectrometers, nuclear magnetic resonance spectrometers, and optical spectrometers.

It is thus a feature of at least one embodiment of the invention to take advantage of current sophisticated sensor technology in improving healthcare delivery.

The point-of-delivery drug Verification apparatus may further include a medical pump for delivery of the drug to the patient and communicating with the computer, and the output may control the medical pump to prevent delivery of drug to the patient when an alert is output.

It is thus a feature of at least one embodiment of the invention to provide close cooperation between delivery drug auditing and drug delivery pumps to better react immediately to possible medication errors.

The sensor system may receive an IV line passing through the medical pump to conduct the drug to the patient.

It is thus a feature coat least one embodiment of the invention to integrate the sensor system into currently employed medical pumps to leverage existing pump technology for auditing drug use.

The sensor system may employ a specially treated IV line having an inner surface interacting with the drug.

It is thus a feature of at least one embodiment of the invention to provide sophisticated analysis of delivered medicines while preserving sterility through the use of disposable IV lines having sensing treatment, for example, to provide surface enhanced Ramen spectroscopy, chemical reactants, or the like.

The sensor system may associate the package with a measured drug signature and the electronic computer may use the measured drug signature associated with the package for comparison to the correct drug signature.

It is thus a feature of at least one embodiment of the invention to permit use of a separate shared appliance that assesses measured drug signatures that are then linked to packages provided to medical pumps performing the final comparison step.

The association of the package with the measured drug signature may write the measured drug signature to a label on the package.

It is thus a feature of at least one embodiment of the invention to provide a simple method of communicating audit results from a separate shared appliance to individual pumps making use of drug type reading systems contemplated for such pumps.

The association of the package with a measured drug signature may include a timestamp and the computer may further control the medical pump to prevent delivery of drug to the patient when the timestamp has expired before initiation of the delivery.

It is thus a feature of at least one embodiment of the invention to reduce the risk of tampering when there is a transfer of drugs between the sensor system and the pump at the point-of-delivery. The timestamp may be a relatively short time necessary for the transfer process.

The point-of-delivery drug verification apparatus may further include a network circuit for communicating with a remote electronic medical record system identifying a patient, prescribed drug, and prescription expiration for the prescribed drug, and the correct drug signature may be determined from the remote electronic medical record system.

It is thus a feature of at least one embodiment of the invention to provide a central server for drug signatures allowing a wide variety of different types of drugs to be audited.

The remote electronic medical record system may communicate the prescription expiration for the prescribed drug in this information may be used by the medical pump to prevent delivery of drug to the patient when the prescription expiration has passed.

It is thus a feature of at, least one embodiment of the invention to further audit medicine delivery with respect to timeliness.

The electronic computer may communicate through the network circuit with the remote electronic medical record system to provide the identity of the patient to obtain information providing the correct drug signature.

It is thus a feature of at least one embodiment of the invention to provide a simple index structure for obtaining correct drug signature information.

The output may be provided through the communication circuit to the remote electronic medical record system for recordation in the electronic medical record system.

It is thus a feature of at least one embodiment of the invention to provide an audit record of medicine delivery tied to point-of-delivery analysis of the medicine.

The point-of-delivery drug verification apparatus may further include input for identifying an operator of the delivery drug verification apparatus allowing the output to be used to confirm a destruction of the drug by the operator recorded in the electronic medical record.

It is thus a feature of at least one embodiment of the invention to provide an auditing mechanism for end-of-life destruction of medicines by designated individuals.

It should be understood that the invention is not limited in its application to the details of construction and arrangements of the components set forth herein. The invention is capable of other embodiments and of being practiced or carried out in various ways. Variations and modifications of the foregoing are within the scope of the present invention. It also being understood that the invention disclosed and defined herein extends to all alternative combinations of two or more of the individual features mentioned or evident from the text and/or drawings. All of these different combinations constitute various alternative aspects of the present invention. The embodiments described herein explain the best modes known for practicing the invention and will enable others skilled in the art to utilize the invention.

DETAILED DESCRIPTION OF THE PREFERRED EMBODIMENT

Figure 1:
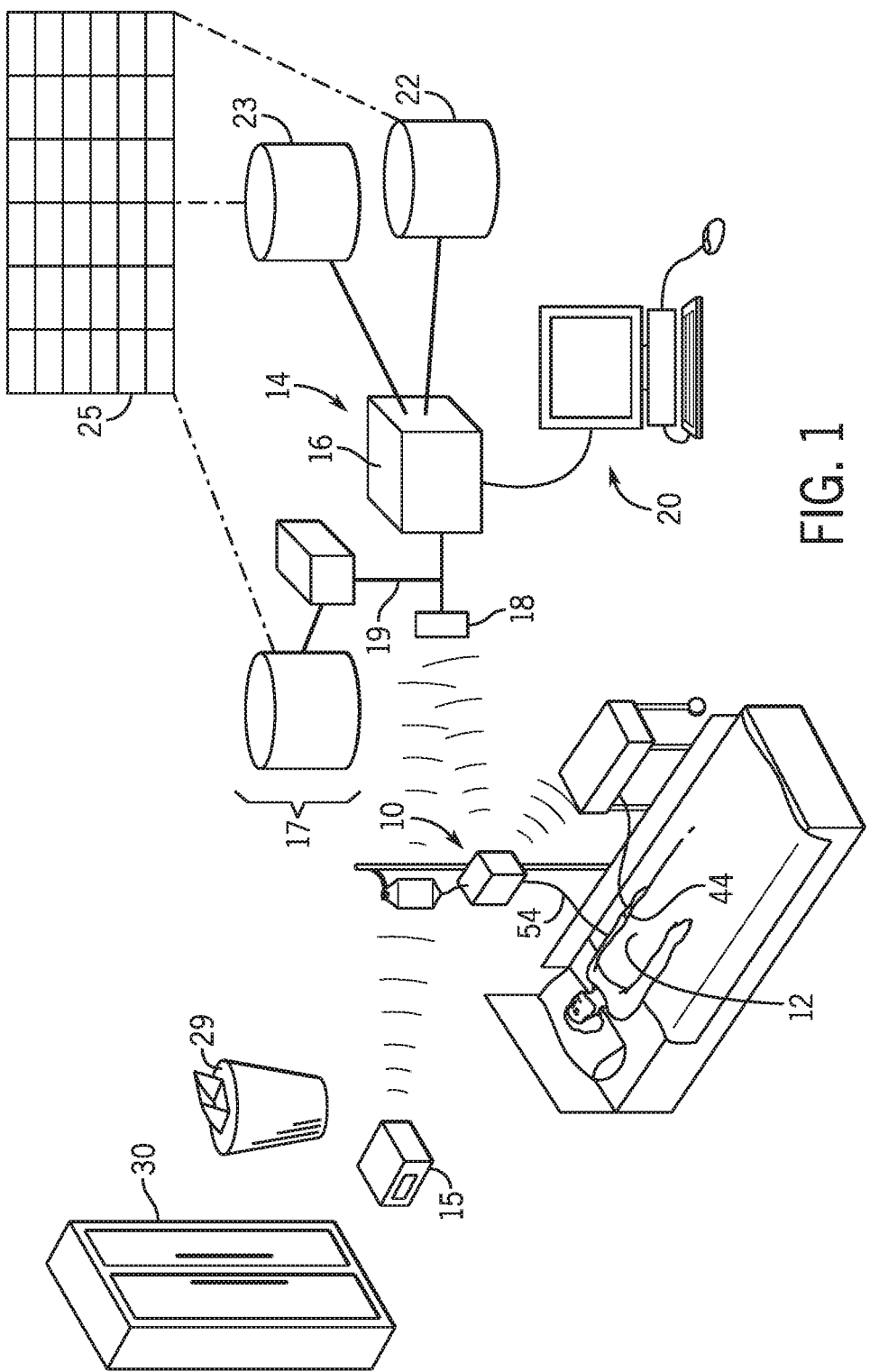
FIG. 1 is a simplified representation of the hospital environment showing a medical pump and a medicine verification appliance receiving information from a central medical records system holding an electronic medical record file.

Referring now to FIG. 1, medical pump 10 may be positioned adjacent to a patient 12 for delivering medicine to a patient. The medical pump 10, as depicted, may be a peristaltic infusion pump or a syringe pump or other similar device for the delivery of medicine to the patient under computerized control.

Each given medical pump 10 may communicate with databases of a central medical record system 14 in the healthcare facility or an external medical database 17 (for example, managed by a third-party) via the internet 19. This communication may be by a variety of means including electrical or optical cables or, as shown, wireless communication, or a combination of both.

The central medical record system 14 may, for example, provide a medical record server 16 communicating via wireless transceiver 18 with the medical pumps 10 and by a standard network circuit or the like with multiple data terminals 20 that may be staffed by healthcare personnel. The healthcare personnel may enter or access patient medical information and read alerts and monitor operation of the medical pumps 10 or the like.

The medical record server 16 may communicate with an electronic medical database 22 holding patient medical records linked to patient identification numbers. As a general matter, medical database 22 will link a patient identifier uniquely identifying a patient with various clinical information about the patient including; weight, height, gender, age, disease, therapy, allergies and the like.

The medical record server 16 may also communicate with a drug database 23 with information regarding "pharmacy orders" for specific drugs for particular patients. In the case of treating the patient by the introduction of a liquid medicament, for example, using a medical pump 10, the drug database 23 may hold data indicating types of drugs (e.g., their chemical identity), their formulation (e.g., concentration or delivery medium), and their preferred delivery rates in rate and total quantity as a function of particular static predicate data (such as patient gender or weight) and real-time predicate data such as blood pressure, glucose level and the like. Some or all of this information may also be obtained to the external medical database 17

The drug database 23 or external medical database 17 may also hold signature characteristics of the drugs being measurable parameters of the drug that reflect the drug type and formulation. As will be discussed further below, the signature characteristics of the drug will be a function of the drug chemical composition, concentration and amount but do not necessarily provide unique identification of those qualities but rather represent a simplified set of data points suitable for auditing.

Generally the drug database 23 is linked to the electronic medical database 22 to receive pharmacy orders, for example, from physicians and linked to a pharmacy system allowing a pharmacist or other dispenser to receive the pharmacy orders to fill them and to mark them as dispensed. The drug database 23 may provide for inventory control as is generally understood in the art. It will be appreciated that the drug database 23 alternatively may be incorporated into the electronic medical database 22.

The medical database 22, the drug database 23, and the external medical database 17 serve to provide a logical electronic medical record 25, for example providing a logical row for each patient associated with patient information (patient ID, name, weight, height, gender, age, disease, therapy, allergies and the like), medicine delivery orders, order expiration dates (prescription expiration dates), chemical, concentration, and amount signatures for the medicines to be delivered, and audit logs of release of the drugs from the pharmacy, the delivery of the drugs to the patient or the destruction of those drugs.

Infusion pumps that may communicate with centralized databases suitable for use with the present invention are described in U.S. Pat. Nos. 8,652,093, 8,945,043 and 8,469,933, all hereby incorporated by reference. Syringe pumps suitable for use with the present invention are described in co-pending patent application Ser. No. 13/659,619 filed Oct. 24, 2012, and entitled: "Syringe Pump with Improved Flow Monitoring" hereby incorporated in its entirety by reference.

Referring still to FIG. 1, the wireless transceiver 18, in one embodiment, may also communicate with a freestanding medicine verification appliance 15, for example, so that the medicine verification appliance 15 may wirelessly exchange data with the drug database 23 and the central electronic medical database 22 in the same manner as the medical pumps 10. The medicine verification appliance 15 may be positioned so as to be shared among nearby medical pumps 10 and/or to be proximate to a medicine repository 30 either being a dispenser of drugs or a storage area for drugs that have been dispensed. Ideally the medicine verification appliance 15 is close enough to the patients 12 that medicine can be verified immediately before administration. Alternatively or in addition, the medicine verification appliance 15 may be positioned near a secured disposal container 29 so that the medicine verification appliance may be used to verify proper disposal of unused or expired medicines by authorized individuals.

Figure 2:
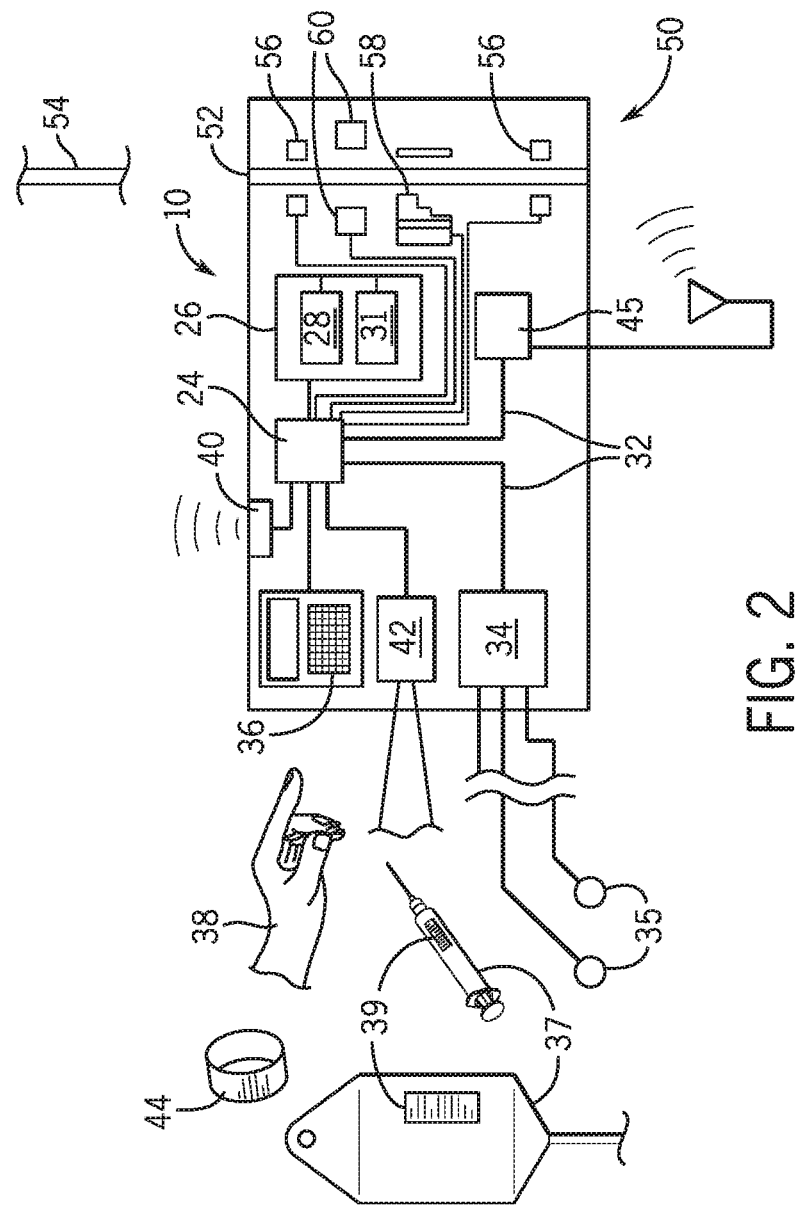
FIG. 2 is a block diagram of the functional components of the medical pump of FIG. 1 according to one embodiment of the invention in which the medical pump provides real-time medicine signature analysis.

Referring now to FIG. 2, the medical pumps 10 may generally include a processor 24 communicating with a memory 26, the latter holding a program 28 providing an operating system for the medical pump 10 and specific executable programs for medicine verification as will be described below. The memory 26 may also hold data structures 31 used by the program 28 as will be described below.

The processor 24 may communicate via various I/O lines 32 which also allow the processor 24 to control or monitor different components of the medical pump 10 including an interface 34 to local patient monitors 35. Such patient monitors may include, for example, sensors measuring blood oxygen, blood pressure, pulse rate, respiration, ECG and patient temperature and may be used to provide for improved automatic control of the medicine being delivered by the medical pump 10 including, for example, painkillers, antibiotics, chemotherapy, anesthesia agents and the like.

The processor 24 may also communicate with a data entry keypad 36, for example, a membrane switch array, allowing data to be entered by medical personnel 38 associated with a particular task to be executed by the medical pump 10. The data entry keypad 36 may be associated with an output screen (such as an LCD alphanumeric display) for facilitating the data entry and review and for providing output to medical personnel 38. A more advanced touch screen may be used for inputting and displaying information. The data entry keypad 36, for example, may be used to enter patient identification information, medicine information, and medicine delivery rate or volume, in the case of a medical pump.

The processor 24 may further communicate with a context sensor 42 which may provide important contextual information about the environment of the medical pump 10. Context sensor 42 may, for example, be an RFID tag reader for reading labels 39 on medicine containers 37, for example, as held in an IV bag or syringe or held in a wristband 44 on the patient 12 (shown in FIG. 1). Alternatively, the context sensor 40 may be a barcode reader, for example, for scanning a barcode label 39 on the medicine containers and wristband 44 on a patient 12 (shown in FIG. 1), or the IV bag or syringe medicine containers 37 or the like. The wristband 44 may provide for a patient identification number that may be used to index one or both of the medical database 22 and drug database 23 (or the electronic medical record 25).

The labels 39 on the medicine containers 37 may include nominal medicine type and concentration or other formulation details of the drug in the container 37 and may further include an intended date of delivery and patient identifier identifying the patient to receive the drug. In some embodiments, the labels 39 may indicate a measured signature of the drug obtained from the separate medicine verification appliance 15. It will be understood that the labels 39 need not actually contain the described information but may alternatively provide an index to the drug database 23 or medical database 22 (or the electronic medical record 25) as discussed above so that this information may be retrieved wirelessly. When the labels 39 contain the actual information or link to that information through a separate database, the packages are effectively associated with the data printed on or linked to the label.

The processor 24 may also communicate with a wireless transceiver 45, for example, a ZigBee®, Wi-Fi, Bluetooth®, Near Field Communication (NFC) or 3G device suitable for communicating with the other medical pumps 10 and/or the wireless transceiver 18 of the medical record server 16. The wireless transceiver 45 may also be used to communicate with the patient monitors 35.

Referring still to FIG. 2, the medical pump 10 may include a pump section 50, for example, for an IV pump, the pump section 50 providing a channel to receive an IV line 54 therethrough. Positioned across the channel 52 may be one or more sensors 56, for example, for detecting fluid pressure, bubbles, and the presence or absence of the IV line 54 itself. These sensors may communicate with the processor 24 which may control a pump actuator element 58, for example, being a peristaltic pump mechanism, that may pump liquid through the IV line 54 by a series of progressive compressions of the IV line 54 in the manner of peristalsis.

Significantly, positioned across the channel 52 may be a medicine signature detector 60 that can evaluate the medicine type and composition of the medicine. In one embodiment, the medicine signature detector 60 may be a compact Raman Spectrometer relying on Raman scattering of a laser projected through the IV line 54 to a corresponding sensor. The IV line 54 may provide a specially prepared window for the purpose of allowing the transmission of the necessary light. Compact Raman spectrometers suitable for this purpose are commercially available through a number of vendors including, for example, Ocean Optics under the tradename of IDRaman mini handheld Raman spectrometer.

Alternatively, the medicine signature detector 60 may make use of a variety of other sensor technologies including but not limited to: surface enhanced Raman spectroscopy using a treated IV line 54, nuclear magnetic resonance, optical absorption spectroscopy, or other sensing systems. These systems may be used alone or in various combinations. When surface enhanced RAM and spectroscopy is used, the IV line 54 may be specially treated, for example, to provide a drug contacting rough metal surface or nano structure such as plasmonic-magnetic silica nanotubes to enhance the sensitivity of the spectroscope. Other reagents and reactants can be coated on the inner surface of the IV line 54, for example, for the purpose of optical spectroscopic measurements. Generally, the measurements contemplated by the present invention can be performed without breaching the sterile envelope defined by the IV line 54 or the drug container possibly through the use of special windows are optical sections therein.

Generally the medicine signature detector 60 will provide quantitative outputs that permit the development of a multivariable signature related to the medicine type and compounding (concentration, etc.) derived directly from the medicine in the IV line 54. The signatures may, for example, be numeric vectors and will be used to reduce the risk of improper medicine types or wrong concentration of medicine are being delivered to the patient as will be discussed below. In the example of the spectroscope, the signature may be a multipoint spectrum together with a drug package net weight value.

Figure 3:
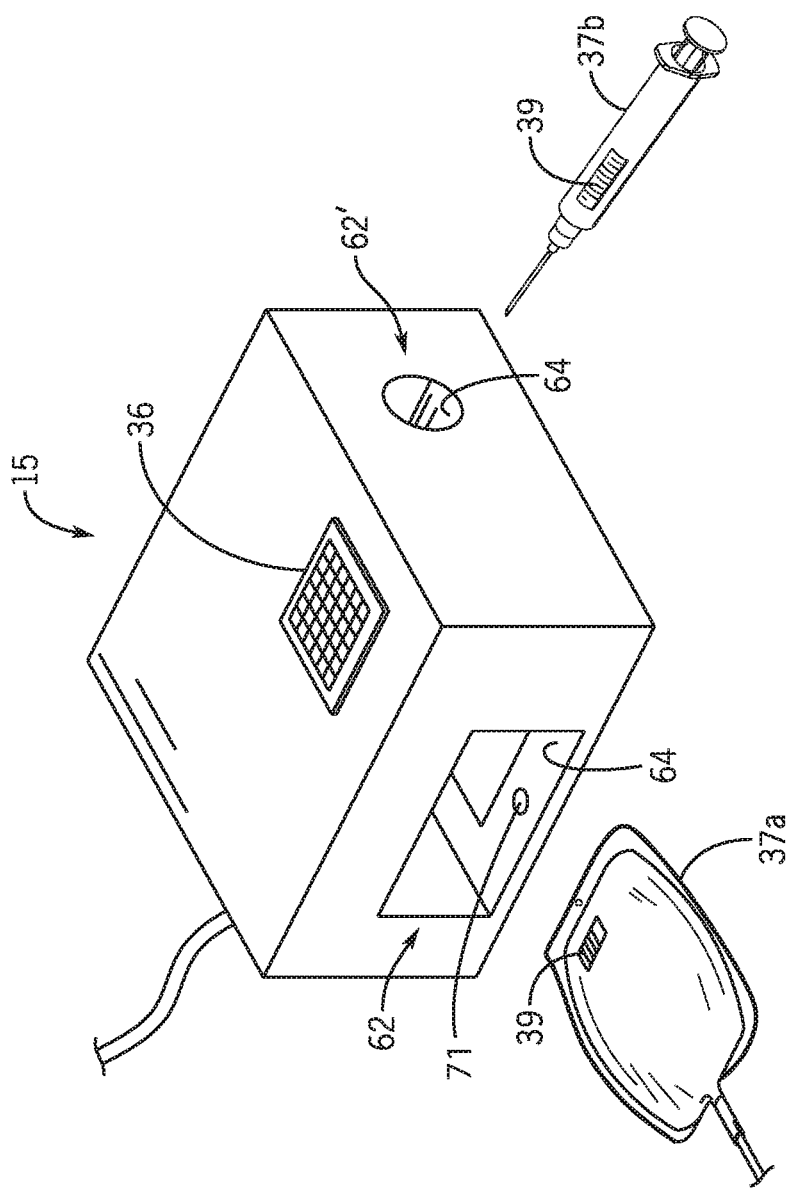
FIG. 3 is a perspective view of a second embodiment of the medicine verification appliance shared among medical pumps for providing contemporaneous medicine signature analysis.
Figure 4:
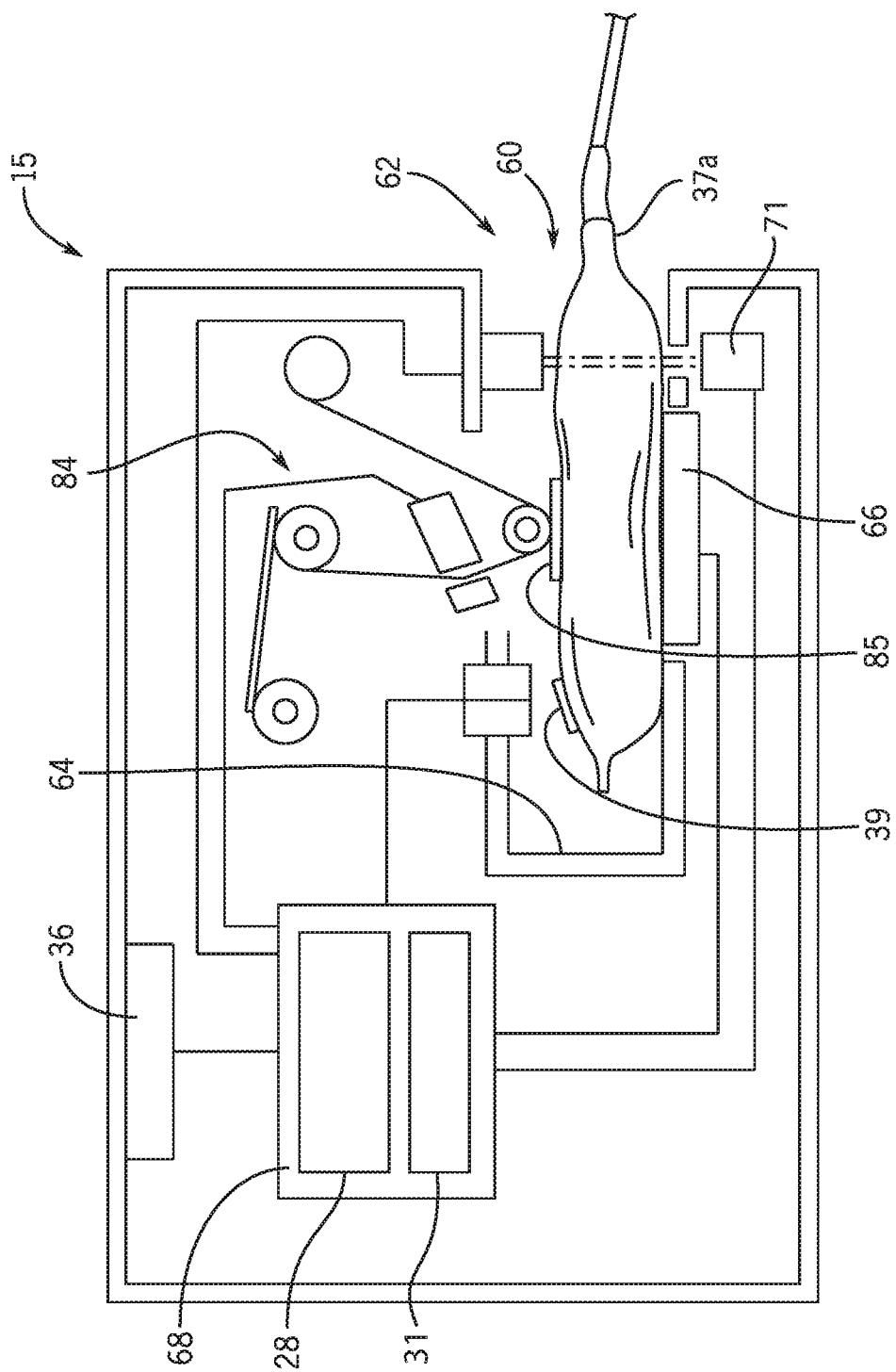
FIG. 4 is a simplified cross-sectional view of the appliance of FIG. 3 showing principle functional components of this appliance.

Referring now to FIGS. 3 and 4, in an alternative embodiment the medicine signature detector 60 may be shared among multiple, proximate medical pumps 10 by using a freestanding medicine verification appliance 15 holding the medicine signature detector 60. This approach reduces the cost of medicine analysis and verification. Generally, in this case, the appliance 15 may provide for entry ports 62 or 62' operating respectively to receive different types of medicine containers 37, for example, with port 62 receiving IV bags 37a and port 62' receiving preloaded medicine syringes 37b within respective analysis chambers 64.

The medicine verification appliance 15 may include a processor 68 holding a stored program 28 and data files 31 to implement the verification process as previously discussed with respect to the embodiment of FIG. 2. This program 28 operates comparably for both of these embodiments and therefore will be described solely with respect to the medicine verification appliance 15.

Within the chamber 64, a reader 71, for example, an RFID reader or barcode reader or the like, may view a label 39 on the container 37 indicating the medicine type, concentration and patient identification along with other possible information including medicine delivery parameters such as flow rate and total volume. In the medical pumps 10 this may be accomplished by a handheld reader or by near field communication with an RFID tag or the like.

Figure 5:
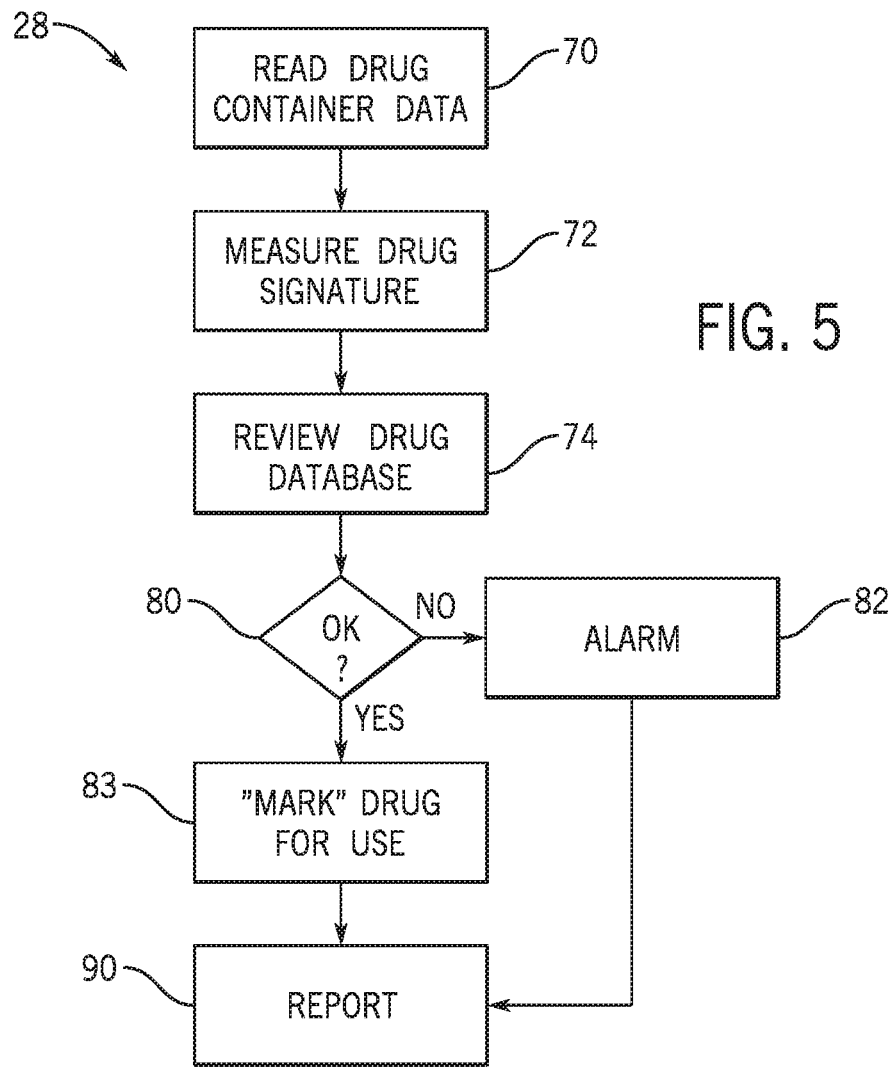
FIG. 5 is a flowchart of the steps of operation of the device of FIGS. 2, 3 and 4 in implementing the present invention to provide patient-specific alerts.

Referring also to FIG. 5, this information may be relayed to the processor 68 as indicated by process block 70.

As indicated by process block 72, parameters of the contained medicine in the container 37a may then be measured to develop a medicine signature. Principally, the signature will be obtained using the medicine signature detector 60 as has been discussed above which may, for example, transmit a laser through the container walls of container 37a to measure the medicine properties including typing concentration. The container 37 may be received on a scale 66 providing a weight to a processor 68 such as may form another component of a signature of the medicine within the container 37.

Figure 6:
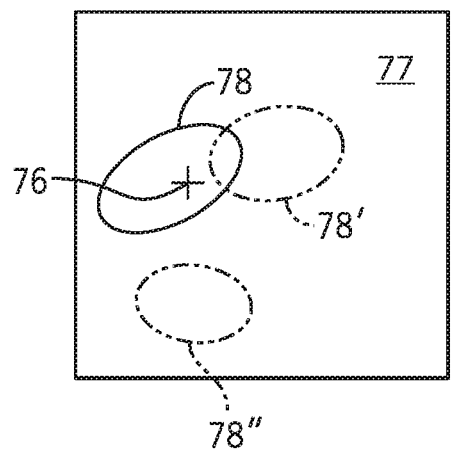
FIG. 6 is a diagram of a signature space showing regions allowing distinctions between drug types and formulations using a multidimensional signature.

Referring momentarily to FIG. 6, the signature ("measured drug signature") will provide a data point 76 generally within an N-dimensional signature space 77 which may include dimensions of weight, Raman spectral peaks and the like. As noted before, Raman spectroscopy may be associated with other sensing techniques described above to include additional dimensions to the signature space 77.

Returning to FIG. 5, information from process block 70 and 72 may then be reviewed at process block 74 against the data obtained from the medical database 22 and drug database 23 (based on the information from process block 70) indicating generally the type and formulation of a medicine to be delivered to the particular patient.

Referring to FIG. 6, this information from the medical database 22 and drug database 23 may be used to identify a signature profile 78 ("correct drug signature") stored in the medical pump 10 or medicine verification appliance 15, or the signature profile 78 may be returned from the drug database 23 to the medical pump 10 or medicine verification appliance 15. The medicine signature profiles 78 also indicate a range within the signature space 77 in which data point 76 must lie in order to verify that the medicine to be delivered to the patient is the same as that indicated in the medical record databases 22 and drug database 23, this latter information derived, for example, from the physicians order or empirically determined and associated with a particular drug.

At decision block 80, if the data point 76 does not lie within the indicated range of a given signature profile 78, an alarm sequence of process block 82 may be entered. This alarm sequence may, for example, provide real time messages to appropriate individuals wirelessly to alert them of an error and/or may provide an alert to the healthcare practitioner 38 attending the patient using the medical pump 10 or medicine verification appliance 15 to provide an alerting tone or message. Manual override by the healthcare practitioner 38 may be possible through the entry of information identifying the healthcare professional which will be recorded for independent review. The alert will eventually be logged into a report and the electronic medical record 25 to provide an audit trail as indicated by process block 90 to be discussed below.

It will be appreciated that the identification provided by the data point 76 need not provide a comprehensive or unique signature for each given medicine and formulation but in fact there can be signature profiles 78' for different drugs that overlap another signature profile 78. This may be readily accommodated with knowledge of the intended medicine and its formulation that is obtained from the electronic medical database 22 or drug database 23 thereby preventing the need to identify medicines and concentrations in isolation. Generally it is necessary only that the signature profiles 78 distinguish among medicines and variations and formulations likely to be confused or to result from tampering. The evaluation of different drugs may also make use of different dimensions of the signature space 77 based on their distinguishing capabilities of those dimensions. It is desirable that the signature space 77 include dimensions that are sensitive not only to medicine type but also medicine concentration so as to be able to detect dilutions and the like as well as total drug amount to detect diversions. For the medical pump 50 of FIG. 2, total drug amount may be determined by a tally of pump volume (determined from the geometric qualities of the IV tube 54 and the operation of the peristaltic pump 58) or a scale may be built into the IV bag hanger using load cell technology or the like.

The matching of decision block 80 may also look for negative signature values associated with negative signature profiles 78" indicating, for example, adulteration or contamination of the medicine, such as common dilutions or the like. In this way the output may indicate not only incorrect medicines but also distinguish among different types of medicine error.

Referring to FIG. 5, if at decision block 80 the data point 76 lies within the indicated range of a signature profile 78, then the proper medicine type and formulation has been established and the medicine may be "marked" for use as indicated by process block 83. In the case of the pump 10 of FIG. 2, this marking may be virtual and applied to the container 37 connected to the IV pump 10 so long as that container 37 or its IV line 54 is not removed indicated by the line sensor or a loss of communication with the label 39 in the case of the near field reader.

In the case of the embodiment of FIG. 4, the marking may be physical by means of a label printer 84 which may print and apply an adhesive label 85 to the container 37 while the container 37 is in the chamber 64 or is data linked to, for example, serial number marked on the drug container and serving as an index to this data stored for example in the electronic medical record 25. The label 85 providing the data or serial number may be a tamper-resistant label as implemented either physically through the use of adhesives on the physical label 85 or may be made virtually tamper-resistant by encoding within a barcode or other optical code of the physical label 85 an encrypted form of information on the label 39 so that when the bag is moved to the pump 10, label 39 and the label 85 applied by the label printer 84 must match in order for the pump 10 to operate without an alarm. The information on the label 85 may be such as to prevent ready counterfeiting of that label, for example, by providing information that is not readily readable by a human and which incorporates information of the label 39, for example, using public-key encryption. It will also be appreciated that the label 85 may be an RFID tag label or may encode information in an RFID tag associated with label 39. Marking such as a fluorescent dye may be placed on the label 39 indicating that the drug container 37 has been used in the marking process to prevent reuse. This can be also accomplished through recording of information from the label 39 in the drug database 23.

Once the labeling process is complete, then at process block 90, information regarding the assessment of the medicine and its delivery may be provided to the remote electronic medical database 22 and drug database 23.

Generally the label 85 or similar information recorded in the medical database 22 and drug database 23 with respect to the label 85 will include a date and time stamp so that the medicine must be delivered to the patient 12 within a predetermined time or else the verification process would need to be repeated. This time may be extremely short for the embodiment of FIG. 2 since the verification may be done on a concurrent or continuous basis and may be as short as five minutes to 30 minutes for the medicine verification appliance 15 of FIG. 1. This delay may be logged in the medical database 22 and drug database 23 and may provide real-time alerts to individuals.

Referring now to FIGS. 1 and 3, the medicine verification appliance 15 may also be used for an end-of-life audit mechanism for disposal of drugs for example in a secured container 29. In this case, authorized individuals may identify themselves using the keypad 36 associated with the appliance 15 indicating that the drug is to be discarded. The drug identity is then confirmed using the sensor system 60 of the appliance 15 linked to for example a serial number on the drug package 37a. The appliance 15 may then compare the measured drug signature to a correct drug signature obtained from the electronic medical record 25 (or this comparison can be performed elsewhere) and provides a label 85 attached to the drug container indicating that the drug is not for use and will be discarded. The authorized individual may then place the drug in the tamperproof secured container 29 providing an end-of-life verification of proper drug disposal by qualified individuals. This disposal is then recorded in the electronic medical record 25.

Certain terminology is used herein for purposes of reference only, and thus is not intended to be limiting. For example, terms such as "upper", "lower", "above", and "below" refer to directions in the drawings to which reference is made. Terms such as "front", "back", "rear", "bottom" and "side", describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context.

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

References to "a microprocessor" and "a processor" or "the microprocessor" and "the processor," can be understood to include one or more microprocessors that can communicate in a stand-alone and/or a distributed environment(s), and can thus be configured to communicate via wired or wireless communications with other processors, where such one or more processor can be configured to operate on one or more processor-controlled devices that can be similar or different devices. Furthermore, references to memory, unless otherwise specified, can include one or more processor-readable and accessible memory elements and/or components that can be internal to the processor-controlled device, external to the processor-controlled device, and can be accessed via a wired or wireless network.

It is specifically intended that the present invention not be limited to the embodiments and illustrations contained herein and the claims should be understood to include modified forms of those embodiments including portions of the embodiments and combinations of elements of different embodiments as come within the scope of the following claims. All of the publications described herein, including patents and non-patent publications, are hereby incorporated herein by reference in their entireties.

What is claimed is:

1. A drug verification apparatus comprising:
    a sensor system adapted to analyze a drug in a package for delivery to a patient by receiving input data and performing spectral analysis to establish a measured drug signature;
    an input for receiving a nominal identity of the drug in the package linked to the package;
    an electronic computer configured to execute a stored program to:
        (1) receive the nominal identity of the drug to determine a correct drug signature associated with the drug from a first data set of correct drug signatures;
        (2) compare the correct drug signature with the measured drug signature to determine whether there is a match;
        (3) receive the nominal identity of the drug to determine negative drug signature profiles associated with commonly known adulterations or contaminations associated with the nominal identity of the drug from a second data set of negative signature profiles wherein the negative drug signature profiles distinguish among different types of drug errors;
        (4) compare the negative drug signature profiles with the measured drug signature to determine whether there is a match; and
        (5) provide an output based on both (a) a comparison between the correct drug signature and the measured drug signature and (b) a comparison between the negative signature profiles and the measured drug signature, the output indicating an adulteration or contamination of the drug if (i) there is no match between the correct drug signature and the measured drug signature and (ii) there is a match between the negative signature profiles and the measured drug signature; and
    a medical pump for delivery of the drug to the patient and communicating with the electronic computer wherein the electronic computer is programmed to control the medical pump to prevent delivery of the drug to the patient when the output is provided, wherein the output includes an alert;
    wherein the sensor system is adapted to receive an intravenous (IV) line passing through the medical pump to conduct the drug to the patient;
    wherein the measured drug signature is a function of a chemical formulation and concentration of the drug; and
    wherein the correct drug signature is non-unique and does not uniquely identify the drug identity when matched.

2. The drug verification apparatus of claim 1 wherein the verification occurs at a point of drug delivery.

3. The drug verification apparatus of claim 1 further including a scale for measuring a weight of the drug and wherein the measured signature and correct signature include weight components.

4. The drug verification apparatus of claim 3 wherein the correct drug signature is a function of both chemical formulation and concentration of the drug.

5. The drug verification apparatus of claim 1 wherein the sensor is a spectrometer.

6. The drug verification apparatus of claim 5 wherein the spectrometer is selected from the group consisting of: Raman spectrometers, surface enhanced Raman spectrometers, nuclear magnetic resonance spectrometers, and optical spectrometers.

7. The drug verification apparatus of claim 6 wherein the spectrometer is a Raman spectrometer.

8. The drug verification apparatus of claim 1 wherein the sensor system employs a treated IV line having an inner surface interacting with the drug.

9. The drug verification apparatus of claim 1 wherein the sensor system associates the package with a measured drug signature and the electronic computer uses the measured drug signature associated with the package for comparison to the correct drug signature.

10. The drug verification apparatus of claim 9 wherein the association of the package with the measured drug signature writes the measured drug signature to a label on the package.

11. The drug verification apparatus of claim 9 wherein the association of the package with the measured drug signature includes a timestamp and wherein the computer further controls the medical pump to prevent delivery of the drug to the patient when the timestamp has expired before initiation of the delivery.

12. The drug verification apparatus of claim 1 wherein the pump is selected from the group consisting of a syringe pump and an infusion pump.

13. The drug verification apparatus of claim 1 further including a network circuit for communicating with a remote electronic medical record system identifying a patient, prescribed drug, and prescription expiration for the prescribed drug.

14. The drug verification apparatus of claim 13 wherein the computer further communicates with the remote electronic medical record system to receive the prescription expiration for the prescribed drug and controls the pump to prevent delivery of the drug to the patient when the prescription expiration has passed.

15. The drug verification apparatus of claim 13 further providing an input for receiving an identity of the patient and wherein the electronic computer communicates through the network circuit with the remote electronic medical record system to provide the identity of the patient to obtain information providing the correct drug signature.

16. The drug verification apparatus of claim 15 wherein the input for receiving the identity of the patient employs an input selected from the group of: an RFID sensor output, a barcode sensor output, and a human machine interface output.

17. The drug verification apparatus of claim 13 wherein the output is provided through the network circuit to the remote electronic medical record system for recordation in the electronic medical record system.

18. The drug verification apparatus of claim 13 further including an input for identifying an operator of the delivery drug verification apparatus and wherein the output is used to confirm a destruction of the drug by the operator recorded in the electronic medical record.

19. The drug verification apparatus of claim 1 wherein the drug verification system includes a plurality of ports for receiving different types of drug packages to be analyzed by the sensor system.

* * * * *